United States Patent [19]

Fennel, III et al.

[11] 4,284,725

[45] Aug. 18, 1981

[54] VIRUS TITRATION AND IDENTIFICATION SYSTEM

[75] Inventors: Robert H. Fennel, III, Walkersville; Robert W. McKinney, Frederick, both of Md.

[73] Assignee: Dynasciences Corporation, Los Angeles, Calif.

[21] Appl. No.: 714,072

[22] Filed: Aug. 13, 1976

[51] Int. Cl.$^3$ .............................................. C12M 1/20
[52] U.S. Cl. ...................................... 435/301; 435/5; 422/99
[58] Field of Search ................ 195/103.5 V, 103.5 M, 195/127, 139, 140, 103.5 A; 435/300, 301, 5

[56] References Cited

U.S. PATENT DOCUMENTS

| | | | |
|---|---|---|---|
| 3,482,943 | 12/1969 | Csizmas et al. | 195/103.5 A |
| 3,649,464 | 3/1972 | Freeman | 195/140 |
| 3,713,985 | 1/1973 | Astle | 195/103.5 M |
| 3,785,928 | 1/1974 | Kessler | 195/139 |
| 3,883,398 | 5/1975 | Ono | 195/127 |

OTHER PUBLICATIONS

Lennette et al., Manual of Clinical Microbiology, 2nd Edition, pp. 672–677 and 691 & 692 (1974).

*Primary Examiner*—Alvin E. Tanenholtz
*Attorney, Agent, or Firm*—Donald E. Nist

[57] ABSTRACT

The improved virus titration and identification system of the present invention comprises a transparent plate having a plurality of spaced wells arranged in a plurality of spaced rows. A dried, preferably freeze-dried, amount of viable specific virus antiserum or a dried, preferably freeze-dried, amount of normal serum is disposed in each well. All wells containing a given specific antiserum are aligned in a single row of a given direction and all of the rows which contain antiserum are aligned with each other.

In one embodiment, the system includes a reference locator disposed on the transparent plate and movable relative thereto. The locator comprises a sheet defining a pair of intersecting light-transmitting windows of specific length. Such windows may be slots in the sheet and may intersect each other at about their mid-points. Preferably, the plate has the wells arranged in a rectangular pattern, so that there are rows of wells in two different orientations at about 90° from each other, the locator windows having the same orientation.

The present method of virus identification includes collecting and isolating a virus to form an isolate, then exposing the isolate in a plurality of separate aliquots at various concentrations to equal amounts of different specific viable virus antisera and normal serum incorporated in the wells of the plate. The aliquots then have equal amounts of test culture cells added to them and incubated in them until a cytopathic effect of the virus being tested in the aliquots can be determined by microscopic observation of the test culture cells, such determination indicating the type and strength of the virus. The contacting, incubation and cytopathic determination called for in the method are most advantageously carried out utilizing the above-identified improved system of the invention.

14 Claims, 5 Drawing Figures

VIRUS TITRATION AND IDENTIFICATION SYSTEM

BACKGROUND

1. Field of the Invention

The present invention generally relates to detection systems and methods and more particularly to improved systems and methods for identifying and determining the concentration of viruses.

2. Prior Art

Viruses constitute a group of infectious agents which are separately identifiable from other infectious microorganisms on the basis of their structure and their mode of replication and antigenicity. Viruses are the smallest infectious agents (20–300 mu. in diameter) containing a molecule of nucleic acid as their genome. The nucleic acid is encased in a protein shell and the entire infectious unit is called a virion. Virions replicate only in living cells. The viral nucleic acid contains information necessary for programming the infected host cell to synthesize a number of specific macro-molecules. Towards the end of this replication cycle more viral nucleic acid and coat proteins are produced, the latter assembling together to form the capsid which encases and stabilizes the viral nucleic acid and facilitates the attachment and penetration of the virus upon contact with new susceptible cells. Viral antiserum neutralizes the virus because it reacts with the antigens of the protein coat.

When a virus infects living animals, specific antibodies are formed and are recoverable in blood serum from the living host. The specific antibodies render the host immune to the antibodies being known as antiserum. If antiserum specific to a given virus is present in a sufficient amount in a test sample which also contains the given virus and tissue cells which can be attacked by that virus, the virus attack is prevented or neutralized by the specific antiserum, thus identifying the virus. Tests based on this concept in determining the identity of viruses are called neutralization tests. Various other serological tests have been devised and are named according to the nature of the changes observed as a result of contacting the antiserum with the virus, i.e., the antibody-antigen reaction. Thus, such tests are called agglutination, precipitation-flocculation tests, and hemagglutination-inhibiting and complement fixation tests, among others. Neutralization tests have proven to be particularly valuable in the identification of viruses.

In the usual types of neutralization tests, the virus to be identified is contacted with various specific antisera of known types, as well as normal serum. Tissue cells are placed into contact with the virus and serum mixtures. After incubation of the test cells plus virus and serum, the cytopathic effect, if any, of the virus on the cells is determined microscopically and indicates the nature of the virus. The cytopathic effect will vary according to the type of cell and the type of virus. Typically, tissue cells when infected by virus exhibit a change in physical shape. Thus, for example, they may tend to become round rather than irregular or they may clump together and/or shrink. If the antiserum present in a given test sample neutralizes the effect of the virus, then the virus is identifiable as being of the same type as caused the elaboration of the antibodies in the antiserum.

In performing a neutralization test, it is usual to first run a series of titers in order to determine the approximate concentration of the virus being tested. This is because most such tests require the use of a known concentration of virus, for example 100 $CPED_{50}$. $CPED_{50}$ means the virus dose which will produce cytopathic effects on test tissue cells in 50% of the cases. In order to determine what dilution of the virus will bring it to a concentration of 100 $CPED_{50}$, a calculation is usually made, based on the titer results, according to the method of Reed & Muench (American Journal of Hygiene 27:493–497, 1938).

Normally, a considerable period of time is required in order to carry out the necessary titration procedure so as to determine the concentration of the virus and thus be able to adjust it to 100 $CPED_{50}$. Further time is required to test the virus in 100 $CPED_{50}$ concentration against various dilutions of various antisera to determine which particular virus is involved. Moreover, substantial amounts of reagents and laboratory equipment and a plurality of skilled personnel are normally involved.

Ways have been sought to improve virus neutralization test procedures so as to reduce their steps and the time, personnel and equipment for carrying them out, thereby reducing their overall cost. Some of the newer neutralization tests employ micro-titration plates which contain a plurality of titration wells for simultaneously running parallel tests. However, these wells must be filled through micro-pipettes with various concentrations of antisera and virus isolates, and in some cases normal sera, in order to perform the test procedures. It has been found that it is relatively difficult, particularly when laboratory time is in short supply, to utilize the micro-titration plates because great care must be taken in transferring the liquid antisera and isolates to the wells to assure their proper dilutions. This is particularly the case when up to 96 or more wells are used in a single micro-titration plate. Attempts to automate such tests have substantially increased costs due to complicated automation equipment and necessary equipment clean-up time for skilled, high salaried personnel.

Accordingly, there remains a need for improved means and procedures for carrying out virus neutralization tests economically, rapidly and efficiently with accuracy.

SUMMARY OF THE INVENTION

The foregoing needs have now been satisfied by the improved virus titration and identification system and method of the present invention. The method and system are substantially as set forth in the Abstract above. The system includes a transparent plate containing a number of spaced wells arranged in a number of rows preferably oriented in two directions. Each well contains dried specific antiserum or dried normal serum. Thus, various specific viable virus antisera in dried form as well as normal serum in dried form are present in different rows in the wells of the plate. Normally, in order to preserve the viability of the antisera and the normal serum, the drying technique is freeze-drying or lyophilization. This can be carried out by first freezing the antiserum or normal serum in the wells of the plate and then, while still in the frozen state, removing moisture therefrom under vacuum. The viable dried antisera and normal serum in the wells are reconstitutable with aliquots of dilutions of the virus isolate to be tested.

The reference locator of the invention preferably utilized with the transparent plate of the invention has windows oriented in two directions and intersecting each other. The window orientation corresponds to the orientation of the rows of wells, so that the locator can be used to help focus the field of search in locating the well or wells which microscopically exhibit a cytopathic effect after test cells have been added to each well and the wells have been incubated. Although the present method can be carried out without utilizing the locator, it is most advantageous to employ the locator so that a maximum of efficiency can be imparted with a maximum of savings in time and cost of materials and so that the results will show the greatest degree of accuracy and reproducibility. Further advantages of the present method and systems are set forth in the following detailed description and accompanying drawings.

DRAWINGS

DETAILED DESCRIPTION

Figure 1:
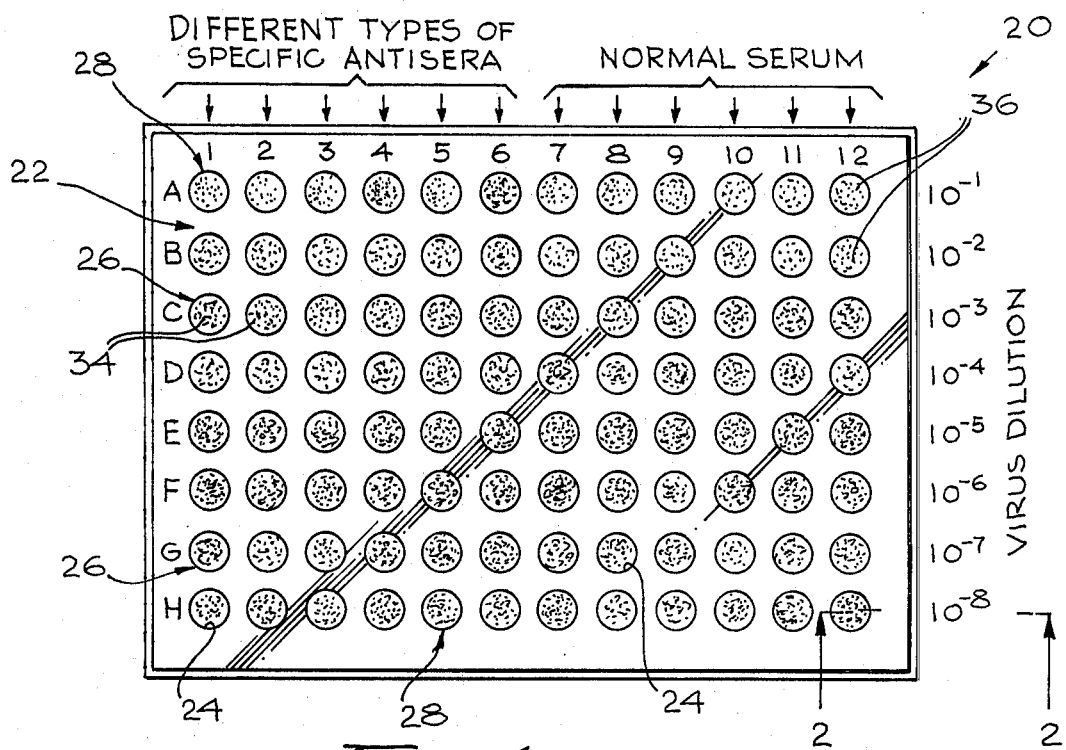
FIG. 1 is a schematic top plan view of a transparent plate utilized in a preferred embodiment of the system of the present invention.
Figure 2:
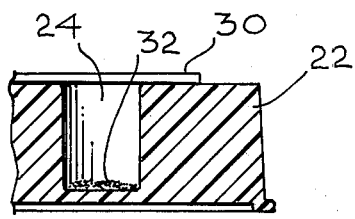
FIG. 2 is a schematic enlarged, fragmentary cross section taken along the section line 2—2 of FIG. 1.

FIGS. 1 and 2

Now referring more particularly to FIG. 1 of the accompanying drawings, a preferred embodiment of the improved virus titration and identification system of the invention is set forth therein in schematic top plan view. Thus, system 20 is depicted which comprises a flat elongated, preferably transparent, plate 22 of, for example, plastic, glass or the like, preferably a plastic such as polystyrene or the like, and for example, about 5 inches × 3½ inches, having a plurality of spaced wells 24 therein arranged in a plurality of spaced rows in two directions to form a grid pattern. A plurality of spaced rows 26 in a first direction are each provided with, for example, horizontal wells 24. The wells 24 of the various rows 26 designated A through H are aligned with one another and the rows 26 are separated from one another, as shown in FIG. 1, to also provide a plurality of spaced rows 28 in a second direction perpendicular to the first direction, for example, vertical rows 28 designated 1–12. In plate 22, as shown in FIG. 1, there are eight rows 26 of twelve wells 24 each for a total of 96 wells. All wells 24 are of the same dimension regardless of location in plate 22.

Each well 24 is more particularly shown in schematic cross section in FIG. 2 and comprises an open-topped, closed bottom circular depression or indentation within plate 22. The wells 24 of plate 22 may be, for example, about 0.25 inches I. D. and may be protected from contamination before use by a cover lid 30 or sheet of, for example, peelable polyethylene or the like (FIG. 2). Each well 24 in plate 22 has provided therein a dried deposit 32 which comprises either dried viral specific antiserum 34 or dried normal serum 36. The concentration of dried antiserum 34 of a specific type is uniform among a plurality of wells 24 containing the same and such wells 24 are arranged in sequence. Thus, in the particular vertical row 28 designated in FIG. 1 by the number 1, one specific type and concentration of antiserum in dried viable form is deposited in each of the sequential wells 24 thereof which are designated A, B, C, E, E, F, G, and H. All wells 24 of vertical row 2 contain a separate dried viable antiserum in the same uniform concentration. Similarly, vertical rows 3, 4, 5 and 6 each contain a different dried viable antiserum in all wells 24 thereof but in that same concentration per well 24, while all wells 24 in the vertical rows 7, 8, 9, 10, 11 and 12 contain that same concentration of dried viable normal serum. Therefore, each horizontal row 26 (rows A, B, C, D, E, F, G and H) has a different dried viable antiserum in each of its wells 1, 2, 3, 4, 5 and 6 and dried viable normal serum in each of its wells 7, 8, 9, 10, 11 and 12, all at the same concentration. Such concentration may be, for example, about 1% serum (before freeze-drying).

The dried aliquots of antisera and normal serum are preferably provided initially by supplying the respective wells 24 in plate 22 with the proper concentration of neutralizing antibody in a suitable medium, such as saline, and the normal serum also in the appropriate concentration, then subjecting the liquid material in wells 24 first to freeze-drying. Freeze-drying, also known as lyophilization, or an equivalent method, is used in order to maintain the viability of the various antisera and the normal serum so dried. Plate 22 can then be packaged so as to seal the wells 24 against contamination and moisture. Thus, sterile plastic sheet 30, shown in FIG. 2, can be applied over and sealed to the top of plate 22 and can be stripped therefrom when plate 22 is to be used.

The type specific antisera which are used in wells 24 of plate 22 can be obtained in any suitable known manner. Techniques will somewhat vary, depending on the organisms involved. For enteroviruses, normally techniques such as those outlined on pp. 553 et seq. of the book entitled Diagnostic Procedure for Viral & Rickettsial Infections by Edwin H. Lennette and Nattialie J. Schmidt (editors), fourth edition, 1969, American Public Health Association, Inc. can be employed. Such antisera are produced, for example, in animals such as monkeys, rabbits, guinea pigs, mice, hamsters, horses, etc. Thus, in the case of monkeys, they may be injected intramuscularly a number of times with tissue culture fluid or mouse tissue infected with a specific enterovirus, such as coxsackie virus B-1. After an interval, they are exsanguinated and the neutralization titer of the serum isolated therefrom is determined. Similar procedures can be used to prepare antisera of Coxsackie B-2, B-3, B-4, B-5 and B-6 viruses, various types of polioviruses, echoviruses, etc. It will be understood that the antisera may be, if desired, for other classes of viruses, such as adenoviruses, rhinoviruses, herpesviruses, cytomegaloviruses, arboviruses, poxviruses, reoviruses, myxoviruses, etc. Usually, plate 22 contains deposits 34 of antisera for closely related strains or types of viruses.

It will be further understood that the use of plate 22 is not limited to virus identification but that it also may be employed for identification of rickettsieal and certain other similar diseases amenable to detection by neutralization techniques. Normal serum isolated from the blood of non-immune animals usually is used as the normal serum for deposits 36 in wells 24 of rows 7 through 12 of plate 22.

The improved method of the present invention for identifying virus isolates comprises collecting a virus specimen and isolating it, preferably in a tissue culture, to form an isolate. Varying dilutions of the virus isolate are then simultaneously exposed to the same concentration of each of several specific known virus antisera and to normal serum in the presence of test culture cells and incubating the mix. The amount of neutralizing antibody or normal antibody in such test cells is the same in each aliquot. The cytopathic effect and neutralization thereof on the test culture cells is then determined as an indication of both the type and strength of the virus. The present method is preferably, but not necessarily, carried out utilizing the above-described micro-virident assay plate 22.

In carrying out the present method, the virus to be determined is collected in any suitable specimen, which will vary depending on the virus and the circumstances. For example, virus specimens have been obtained in pharyngeal washings, feces, cerebrospinal fluid, blood, urine, vesicle fluids, etc. Collection at the right time is important to assure that viable virus is present, for example, during the earliest days of illness or immediately after death.

Such specimens usually must be treated immediately to preserve them, as by freezing or the like, or must be used immediately by growing the virus, as in a laboratory animal (monkey, mouse, etc.) or a tissue culture, to form an isolate. For example, human entroviruses which do not require a living animal for their propagation can usually be cultured and isolated in viable primary monkey kidney cell cultures. Thus, for example, all of B type Coxsackie viruses can be grown in such cultures. The techniques for such growth are spelled out in detail in various texts including, for example, from page 569 on, in the above mentioned book entitled Diagnostic Procedures For Viral and Rickettsial Infections. Growth media for the cell cultures into which the virus specimens have been introduced may comprise, for example, those known as Melnick's Medium A or Medium B (p. 570 supra.) Incubation of the cultures is usually at 35°–37° C. over a period of several days or more. The virus present in the incubated culture and medium can be left therein to form the isolate or, in some instances, separated by centrifugation from solids.

Figure 4:
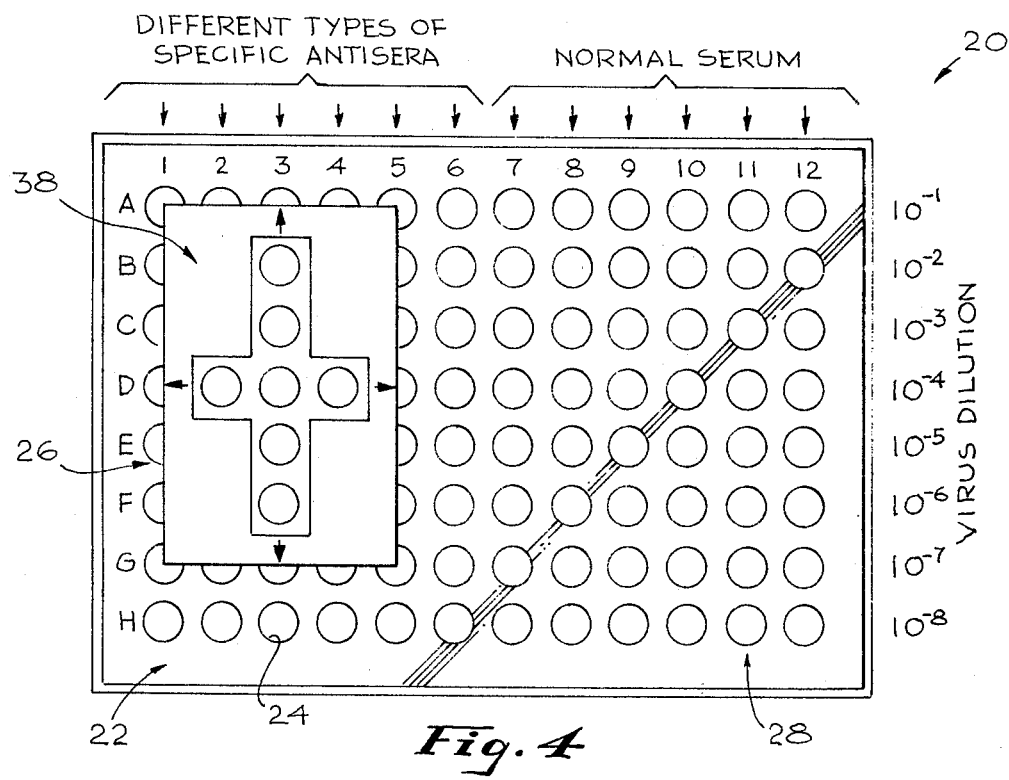
FIG. 4 is a schematic top plan view showing the locator of FIG. 3 in a first position over the plate of FIG. 1; and, FIG. 5 is a schematic top plan view showing the locator of FIG. 3 in a second position over the plate of FIG. 1.

In any event, the resulting isolate containing the virus is then serially diluted, preferably as per the dilution schedule shown in FIGS. 1 and 4, with any suitable dilution medium such as that known as Minimum Essential Medium (Eagle) with Earle's salts (EMEM).

Thus, the isolate may be serially diluted with the above medium, for example, to $10^{-1}, 10^{-2}, 10^{-3}, 10^{-4}, 10^{-5}, 10^{-6}, 10^{-7}$, and $10^{-8}$, each dilution being distributed in equal aliquots to each well 24 in the applicable horizontal row 26 of plate 22. Before such distribution, the dried antisera and normal serum in wells 24 may be reconstituted with any suitable medium such as EMEM. Alternatively, the diluted isolate aliquots can be used as the reconstitution means for the antisera and normal serum.

The mixture in wells 24 preferably is then incubated at about room temperature for about 15–30 minutes, that is, for a time sufficient for the antiserum (in wells 24) which is effective against the virus introduced in the isolate aliquots to neutralize the said virus.

Test indicator cells in a single uniform concentration are then placed in each of wells 24. For example, for the detection of Coxsackie and other enteroviruses, viable Buffalo green monkey kidney cells (BGM cells) in a concentration, for example, of about 15,000 cells/well can be used. The quantity of each aliquot of diluted isolate added to wells 24 may be, for example, about 0.05 ml. when wells 24 are of the size previously described and antisera and normal serum are present in wells 24 in the dried amounts previously described. The wells 24 are then covered and incubated, for example at 35° C., for 24–72 hours, that is, until the cytopathic effect of the virus on the test cells can be determined microscopically. The cytopathic effect of the virus on the test cells will vary, depending on the type of virus, type of test cells and stage of attack, among other factors. However, any substantial abnormality such as rounding or clumping of cells may be viewed as cytopathic effect.

Figure 3:
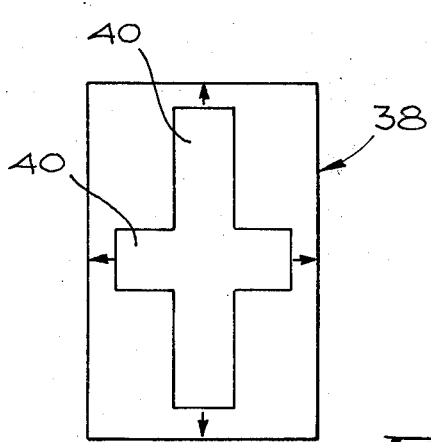
FIG. 3 is a schematic top plan view of a preferred embodiment of a locator utilized with the plate of FIG. 1.
Figure 5:
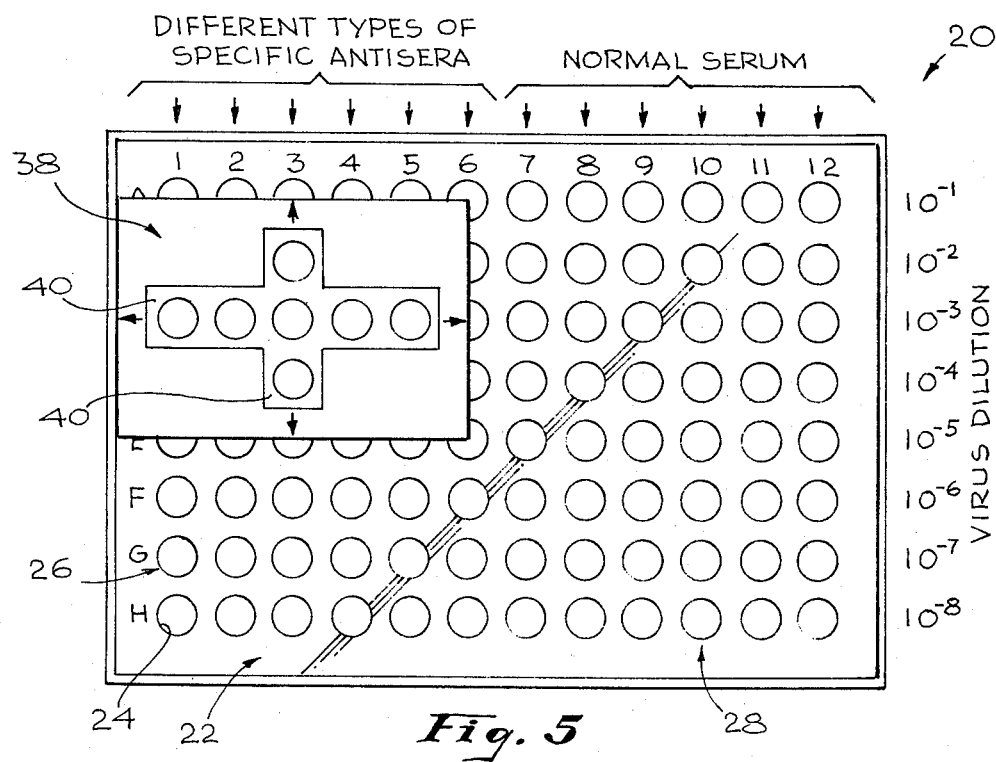

The microscopic examination of wells 24 in plate 22 to determine the cytopathic effect of the virus is facilitated when the novel indicator plate 38, as shown schematically in FIGS. 3, 4 and 5, is utilized. Plate 38 comprises a reference pointer in the form of a thin flat opaque sheet, for example, of plastic, metal or the like having a pair of intersecting light-transmitting windows 40 extending therethrough, as shown in FIGS. 3, 4 and 5. Each window 40 has a width at least that of one of the wells 24 but preferably less than that spanning two adjacent wells 24 and each window 40 has a length sufficient to expose a plurality of wells 24 therethrough. For example, one of the windows 40 may have a length which spans 5 or more adjacent wells in a row while the other of said windows 40 may have a length which may span, for example, three or more adjacent wells in a row intersecting the first mentioned row. Thus, one window 40 allows viewing of wells 24 in a row 26 while the other window simultaneously allows viewing of wells 24 in a row 28. This is clearly shown in FIGS. 4 and 5. The windows 40 preferably intersect at about their centers and are aligned at 90° from each other, that is, in the same orientation as rows 26 and 28. The purpose of the reference pointer 38 is to block off from distracting view the many wells 24 of plate 22 which are not the subject of an immediate examination under the microscope. Plate 38 thus channels attention to selected wells 24. Plate 38 is used by placing over plate 22 and moving it by hand back and forth to sequentially block off various areas of plate 22 from viewing.

In carrying out the microscopic examination, for cytopathic effects, normally the technician first determines the terminal dilution end point of the virus in those wells 24 which contain normal serum by reference to wells 24 in rows 28 designated 7 through 12. This terminal dilution end point is the maximum dilution of the virus which will still produce definite cytopathic effects in the test culture in the presence of normal serum. Usually, three or more of the six wells 24 containing the same virus dilution are required to show the cytopathic effect before it can be stated to be definitely present, that is, results are determined for a $CPED_{50}$ end point. The next greater dilution of virus will cause either no cytopathic effects in the normal serum-containing wells 24 or will cause such an effect in less than 50% of those wells.

When the terminal dilution end point has been determined, neutralization of the virus is read in that horizontal row 26 of wells 24 which contains 100 times the amount of the virus as that contained in wells 24 at the terminal dilution end point. In other words, the reading of the antisera-containing wells is made in a row 26 which contains in each well 24 thereof approximately 100 $CPED_{50}$ of the virus. The one antiserum-containing well 24 in that row 26 which shows no cytopathic effects contains antiserum of the same type as the virus, thereby identifying the virus.

It will be seen that from this procedure essentially simultaneous determination is made of both the strength of the virus, that is, a titration thereof is performed, and the identity of the virus. In conventional methods, these two determinations are separately sequentially made with considerable lengths of time occurring for each determination and with a total length of time for the two determinations, which far exceeds the total length of time used in carrying out the present method. Accordingly, the present method is much faster than conventional methods while still being accurate, simple and convenient. When used with plate 22, preferably also with plate 38, the present method provides optimum results with a minimum expenditure of personnel time and laboratory equipment, supplies, etc. Certain further features of the present invention are illustrated in the following specific examples:

EXAMPLE I

A Coxsackie virus obtained from a stool specimen is cultured in monkey kidney cells at 35° C. for 24–96 hours. The resulting isolate is then serially diluted as follows:

$$10^{-1}, 10^{-2}, 10^{-3}, 10^{-4}, 10^{-5}, 10^{-6}, 10^{-7}, 10^{-8}$$

The culture medium for the monkey cells as well as the dilution medium for the serial dilutions is EMEM. Aliquots of 0.05 ml. each from each of the various serial dilutions are added to wells 24 in plate 22, all aliquots of a given virus dilution being added to all wells in a given horizontal row for example, $10^{-1}$ dilutions in row A. The wells 24 in vertical rows 1, 2, 3, 4, 5 and 6 in plate 22 each have different specific dried antisera for Coxsackie B-1 virus [row 1], Coxsackie B-2 virus [row 2], Coxsackie B-3 virus [row 3], Coxsackie B-4 virus [row 4], Coxsackie B-5 virus [row 5], and Coxsackie B-6 virus [row 6]. The wells 24 in vertical rows 7 through 12 have dried normal serum. All antisera and normal serum are derived from the same animal type, for example a rabbit. All wells in all rows 28 contain the same concentration of antiserum or serum, as the case may be. The addition of the aliquots of the virus dilutions to all wells 24 simultaneously reconstitutes the dried antisera and dried normal serum.

Plate 22 is then incubated at 22° C. for about 30 minutes to allow any neutralization of virus by antiserum to take place, after which indicator cells consisting of Buffalo green monkey kidney cells are added to each well 24 in plate 22 in a concentration of 15,000 cells per well. Plate 22 is then covered and incubated for about 24–72 hours at 35° C., then examined with an inverted microscope. The terminal dilution endpoint of the virus is determined to be in row D (the $10^{-4}$ dilutions) by observing cytopathology in the form of rounded cells in at least 50% of those wells 24 containing normal serum in row D, but essentially no cytopathology for the normal serum-containing wells in row E (the $10^{-5}$ dilutions). The long window 40 in plate 38 is then aligned in a manner to view the antisera wells in row B (the $10^{-2}$ dilutions) and it is determined that only in the case of the well containing Coxsackie virus B-3 antiserum (row 3) is there no observable cytopathology, thereby demonstrating that the virus involved is Coxsackie B-3 virus and that its strength at 100 $CPED_{50}$ is the dilution shown for row B. The total length of time needed to make the described determinations of virus strength and type in plate 22 is approximately 24–48 hours, whereas in the usual neutralization test procedures, those determinations may require more than 168 hours. Accordingly, the present method is not only effective and simple but rapid.

EXAMPLE II

The procedure as set forth in Example I above is utilized for the determination of a polio virus. The specimen from which the isolate is obtained is a stool sample and the isolation procedure comprises inoculating the specimen into a culture and medium comprising primary monkey kidney cells and minimum essential medium and incubating the same at 37° C. for 48–72 hours. The wells of those vertical rows 18 identified as 1, 2 and 3 in plate 22 contain equal volumes, approximately 0.05 ml. of dried type specific polio antisera as follows: In row 1, Type 1, in row 2, Type 2, in row 3, Type 3. All the antisera are derived from immunized monkeys. Aliquots of 0.05 ml. each of the isolate diluted as set forth in Example I are introduced into the wells of plate 12 including those wells of rows 7, 8, 9, 10, 11 and 12, all of which contain dried normal serum in the same volume and from the same type of laboratory animal as the antisera of rows 1 through 3. The terminal dilution endpoint is determined to be that of row E. Accordingly, the wells containing the specific antisera in row E are scanned using locator plate 28 and an inverted microscope and it is determined that only in well 2 of row E is there no cytopathic effect. Thus, the virus is of the same type as the antiserum in that well, type 2 poliovirus.

In parallel tests, the above method is employed successfully in the determination of the following specific viruses using the following specific antisera in the wells of rows 1 through 6, all of which have been derived from the following laboratory animals: Poliovirus types 1 through 3 (rabbit, baboon); Echovirus types 1 through 33 (rabbit, baboon); Coxsackie virus Group B types 1 through 6 (rabbit, baboon); and, Parainfluenza virus types 1 through 3 (guinea pig, rabbit).

Various modifications, changes, alterations and additions can be made in the present method, its steps and parameters and in the present titration and identification system, including the plate and pointer and the aliquots of dried antisera and normal serum therein, their components and their parameters. All such modifications, changes, alterations and additions as are within the scope of the appended claims form part of the present invention.

What is claimed is:

1. An improved virus titration and identification system comprising, in combination:
   (a) a transparent plate having a plurality of spaced wells therein arranged in a plurality of spaced rows in a plurality of orientations;
   (b) a plurality of dried aliquots of viable antisera for specific viruses, said aliquots being disposed in wells in separate ones of said rows, one row of a given orientation for each specific virus; and,
   (c) a plurality of dried aliquots of normal serum disposed in rows in the remainder of said wells.

2. The improved virus titration system of claim 1 wherein said wells are aligned generally in two orientations, said orientations being at about 90° from each other.

3. The improved virus titration system of claim 2 wherein said wells in each said row are aligned and regularly spaced from each other and wherein said rows are aligned and regularly spaced from each other.

4. The improved virus titration system of claim 1 wherein said dried aliquots of specific antisera are freeze-dried and of about equal neutralization strength.

5. The improved virus titration system of claim 4 wherein said dried aliquots of normal serum are freeze-dried and of about equal strength.

6. The improved virus titration system of claim 5 wherein said freeze-dried aliquots of specific antisera in each row of a given orientation are in sequence.

7. The improved virus titration system of claim 1 wherein said system includes a reference locator disposed on said transparent plate and movable relative thereto, said locator comprising a sheet defining a pair of intersecting light-transmitting windows, each said window being at least the width of one of said wells but less than about the width between two adjacent of said wells, each said window being at least a length sufficient to expose a plurality of said wells therethrough.

8. The improved virus titration system of claim 7 wherein said windows comprise slots, wherein said sheet is flat and wherein said slots intersect at about their centers and are aligned at 90° from each other.

9. The improved virus titration system of claim 2 wherein said system includes a reference locator disposed on said transparent plate and movable relative thereto, said locator comprising a sheet defining a pair of intersecting light-transmitting windows, each said window being at least the width of one of said wells but less than about the width between two adjacent of said wells, each said window being at least a length sufficient to expose a plurality of said wells therethrough.

10. The improved virus titration system of claim 1 wherein said windows comprise slots, wherein said sheet is flat and wherein said slots intersect at about their centers and are aligned at 90° from each other.

11. The improved virus titration system of claim 6 wherein said rows constitute horizontal and vertical rows and wherein a plurality of said specific antisera in aliquots and said normal serum in aliquots are disposed in the same rows aligned in one of said two directions.

12. The improved virus titration system of claim 11 wherein said specific antisera aliquots of each row in a given direction are aligned with the specific antisera aliquots of each other row in the same direction.

13. The improved virus titration system of claim 12 wherein said system includes a reference locator disposed on said transparent plate and movable relative thereto, said locator comprising a sheet defining a pair of intersecting light-transmitting windows, each said window being at least the width of one of said wells, but less than about the width between two adjacent of said wells, each said window being at least a length sufficient to expose a plurality of said wells therethrough.

14. The improved virus titration system of claim 13 wherein said windows comprise slots, wherein said sheet is flat and wherein said slots intersect at about their centers and are aligned at 90° from each other.

* * * * *